(12) United States Patent
Alland et al.

(10) Patent No.: US 8,673,930 B2
(45) Date of Patent: *Mar. 18, 2014

(54) PYRIMIDYLAMINOBENZAMIDE DERIVATIVES FOR SYSTEMIC MASTOCYTOSIS

(75) Inventors: Leila Alland, Chatham, NJ (US); Doriano Fabbro, Arlesheim (CH); Jürgen Mestan, Denzlingen (DE); Paul W Manley, Arlesheim (CH)

(73) Assignee: Novartis AG, Basel (CH)

( * ) Notice: Subject to any disclaimer, the term of this patent is extended or adjusted under 35 U.S.C. 154(b) by 135 days.

This patent is subject to a terminal disclaimer.

(21) Appl. No.: 12/769,734

(22) Filed: Apr. 29, 2010

(65) Prior Publication Data

US 2010/0210673 A1 Aug. 19, 2010

Related U.S. Application Data

(63) Continuation of application No. 11/911,575, filed as application No. PCT/US2006/016541 on May 1, 2006, now abandoned.

(60) Provisional application No. 60/676,740, filed on May 2, 2005.

(51) Int. Cl.
*A61K 31/506* (2006.01)
*C07D 401/14* (2006.01)
*C07D 213/38* (2006.01)

(52) U.S. Cl.
USPC .......................................... 514/275; 544/331

(58) Field of Classification Search
None
See application file for complete search history.

(56) References Cited

U.S. PATENT DOCUMENTS

| | | | |
|---|---|---|---|
| 5,521,184 | A | 5/1996 | Zimmermann |
| 5,543,520 | A | 8/1996 | Zimmermann |
| 6,107,301 | A | 8/2000 | Aldrich et al. |
| 7,169,791 | B2 | 1/2007 | Breitenstein et al. |
| 2004/0157855 | A1 | 8/2004 | Heinrich et al. |
| 2005/0054617 | A1 | 3/2005 | Moussy et al. |
| 2005/0095237 | A1* | 5/2005 | Emtage ...................... 424/131.1 |
| 2007/0213317 | A1 | 9/2007 | Buchdunger et al. |
| 2007/0299049 | A1 | 12/2007 | Coutre |
| 2008/0096864 | A1 | 4/2008 | Dimitrijevic et al. |
| 2010/0179179 | A1 | 7/2010 | Buchdunger et al. |

FOREIGN PATENT DOCUMENTS

| | | |
|---|---|---|
| EP | 564409 | 1/2000 |
| WO | 95/09847 | 4/1995 |
| WO | 95/09852 | 4/1995 |
| WO | 97/19065 | 5/1997 |
| WO | WO98/35958 | 8/1998 |
| WO | 98/55152 | 12/1998 |
| WO | 99/03854 | 1/1999 |
| WO | 99/25372 | 5/1999 |
| WO | WO03/007924 A2 | 1/2003 |
| WO | WO 03/076660 A | 9/2003 |
| WO | 2004/005281 | 1/2004 |
| WO | WO 2004/032935 A1 | 4/2004 |
| WO | 2005/049032 | 6/2005 |

OTHER PUBLICATIONS

Tefferi et al.(Inter J Hemato, 79:441-447, 2004).*
Cecil Textbook of Medicine, edited by Bennet, J.C., and Plum F., 20$^{th}$ edition, vol. 1, 1004-1010, 1996.
Gotlib et al., "PKC412, inhibitor of the KIT tyrosine kinase, demonstrates efficacy in mast cell leukemia with the D816V kIT mutation,"Blood, vol. 102(11), p. 919A (2003). XP-001194849.
Stone et al., "PKC412, an oral FLT3 inhibitor, has activity in mutant FLT3 acute myeloid leukemia (AML): A phase II clinical trial ," Blood, vol. 100(11), abstract No. 316 (2002) XP-002320794.
Wang et al., "Pharmacokinetics and pharmacodynamics of PKC412, a FLT3 receptor inhibitor, following oral doses in acute myeloid leukemia (AML) patients," Blood, vol. 102(11) (2003) Abstract XP-002320795.
Weisberg et al., "Inhibition of mutant FLT3 receptors in leukemia cells by the small molecule tyrosine kinase inhibitor PKC42," Cancer Cell, vol. 1(5), pp. 433-443 (2002).
Knapper et al., "The in vito sensitivity of primary AML blasts to two flt3 inhibitors and cytarabine appears independent of flt3 mutation status," Blood, vol. 102(11) p. 24a (2003) Abstract.
Estey Elihu et al., "A randomized phase II trial of the tyrosine kinase inhibitor PKC412 in patients (pts) with acute myeloid leukemia (AML)/high-risk myelodysplastic syndromes (MDS) characterized by wild-type (WT) or mutated FLT3," Blood, vol. 102(11) pp. 614a-615a (2003) Abstract XP-0230797.
Giles F. J., "New drugs in acute myeloid leukemia," Current Oncology Reports, Current Science, GB, vol. 4(5), pp. 369-374 (2002).
Roboz et al., "Phase I trial of PTK787/ZK 222584, an inhibitor of vascular endothlial growth factor receptor tyrosine kinases, in acute myeloid leukemia and myelodysplastic syndrome," Blood, vol. 100 (11), Abstract No. 1308 (2002) XP009025184.
De Bont et al., "Decreased in-vitro cellular drug resistance by addition of vascular endothelial growth factor receptor (VEGFR) inhibitor, PTK787/ZK 222584, to conventional chemotherapy in pediatric AML," Leukemia, vol. 17(3), p. 668 (2003) Abstract XP-002320793.
Bold et al., "New Anilinophthalazines as Potent and Orally Well Absorbed Inhibitors of the VEGF Receptor Tyrosine Kinases Useful as Antagonists of Tumor-Driven Angiogenesis", Journal of Medicinal Chemistry, vol. 43 No. 12, 2000, pp. 2310-2323 XP000971347.
Sakuma et al., << Alterations of the c-Kit gene in testicular germ cell tumors >>, Cancer Science, vol. 94, No. 6, Jun. 2003, pp. 486-491 XP002472363.
Cools et al., "PKC412 overcome resistance to imatinib in a murine model of FIP1L1-PDGFR alpha-induced myeloproliferative disease", Cancer Cell, vol. 3, No. 5, pp. 459-469, May 2003 XP008039395.

(Continued)

*Primary Examiner* — Bong-Sook Baek
(74) *Attorney, Agent, or Firm* — Stephen Johnson

(57) ABSTRACT

The present invention relates to the use of pyrimidylaminobenzamide derivatives for the preparation of a drug for the treatment of systemic mastocytosis.

5 Claims, No Drawings

(56) References Cited

OTHER PUBLICATIONS

Ugo Testa, "Kit mutations in cancer and their treatment with protein kinase inhibitors", Drugs of the Future, 2008, vol. 33(2), pp. 161-174.
Roberts et al. "Resistance to c-kit kinase inhibitors conferred by V654A mutation", Mol. Cancer Therapy. 2007, 6(3), pp. 1159-1165.
Lacal et al., "Changing the course of oncogenesis: The development of tyrosine kinase inhibitors", 2006, EJC Supplements 4, pp. 14-20, 2006.
Freshney, "Culture of Animal Cells, A Manual of Basic Technique", Alan R. Liss, Inc., New York, p. 4, 1983.
Dermer, "Another Anniversary for the War on Cancer", Bio/Technology, vol. 12, pp. 320, 1994.
MSNBC News services "Mixed results on new cancer drug", pp. 1-5, 1983.
Gura, "Systems for identifying New Drugs are Often Faulty", Science, vol. 278, pp. 1041-1042, Nov. 7, 1997.
Ning et al, "Activating mutations of c-kit at condon 816 confer drug resistance in human leukemia cells", Leuk Lymphoma, vol. 41(5-6), pp. 513-522, 2001.
Armstrong et al: Inhibition of FLT3 in MLL: Validation of a therapeutic target identified by gene expression based classification, Cancer Cell, vol. 3, pp. 173-183, Feb. 2003.
Antonescu et al, "Association of KIT Exon 9 Mutations with Nongastric Primary Site and Aggressive Behavior KIT Mutation Analysis and Clinical Correlates of 120 Gastrointestinal Stromal Tumors", Clinical Cancer Research, vol. 9, pp. 3329-3337, Aug. 15, 2003.
Looijenga et al, "Stem Cell Factor Receptor (c-KIT) Codon 816 Mutations Predict Development of Bilateral Testicular Germ-Cell Tumors", Cancer Research, No. 63, pp. 7676-7678, Nov. 15, 2003.
Algros et al., "Small intestinal stromal tumors with skenoid fibers. Clinicopathological study of three cases", Ann Chir. 2003: 128(6): 397-401 abstract, on-line [found in the internet under www.pubmed.com Aug. 7, 2008], PMID: 12943839 [PubMed—indexed for Medline].
Giles, F et al. "A Phase 1/11 Study of AMN107, a Novel Aminopyrimidine Inhibitor of Bcr-Abl, on a Continuous Daily dosing Schedule in Adult Patients (pts) with Imatinib-resistant Advanced Phase Chronic Myeloid Leukemia (CML) or Relapsed/Refractory Philadelphia Chromosome (Ph+) Acute Llymphocytic Leudemia (ALL).", Blood, (ASH Annual Meeting Abstracts), vol. 104, Abstract 22, (2004).
Zermati, Y et al. "Effects of the tyrosine kinase inhibitor STI 571 on the kinase activity of wild type and various mutated c-kit receptors found in mast cell neoplasms," Publ. ASH (2000).
Heinrich C et al. "Inhibition of c-kit receptor tyrosine kinase activity by STI 571, a selective tyrosine kinase inhibitor.", Blood, vol. 96, No. 3, pp. 925-931 (2000).
Akin C et al. Effects of the tyrosine-kinase inhibitor STI571 on mutated kit and neoplastic mast cells. Blood, vol. 96 (11), pp. 747a, Abstract #3231 (2000).
Wedemeyer J et al. "Roles of mast cells and basophils in innate and acquired immunity", Current Opinion in Immunology, vol. 12 (6), pp. 624-631 (2000).
Secor V H et al. "Mast cells are essential for early onset and severe disease in a murine model of multiple sclerosis", The Journal of Experimental Medicine, vol. 191, No. 5, pp. 813-821 (2000).
Berlin A A et al. "Treatment of cockroach allergen asthma model with Imatinib Attenuates Airway Responses.", Am. J. Respir. Crit. Care Med., vol. 171, pp. 35-39 (2005).
London C A et al. "Spontaneous canine mast cell tumors express tandem duplications in the proto-oncogene c-kit.", Experimental Hematology 27, pp. 687-697 (1999).
Ma Y et al. Clustering of activating mutations in c-KIT's Juxtamembrane coding region in Canine Mast Cell Neoplasms., J. Invest. Dermatol. 112, pp. 165-170 (1999).
Ma Y et al. Indolinone derivatives inhibit constitutively activated KIT Mutants and Kill Neoplastic Mast Cells,J. Invest. Dermatol. 114, pp. 392-394 (2000).
Longley B J et al. "Classes of c-KIT activating mutations: proposed mechanisms of action and implications for disease classification and therapy", Leukemia Research 25, pp. 571-576 (2001).
Longley B J et al. "Activating and dominant inactivating c-KIT catalytic domain mutations in distinct clinical foms of human mastocytosis", Proc. Natl. Acad. Sci. USA, vol. 96, pp. 1609-1614 (1999).
Beghini, A et al. "c-kit Activating Mutations and Mast Cell Proliferation in Human Leukemia". Correspondence, pp. 701-702.
Akin C et al., "Soluble stem cell factor receptor (CD117) and IL-2 receptor alpha chain (CD25) levels in the plasma of patients with mastocytosis: relationships to disease severity and bone marrow pathology.", Blood, vol. 96, No. 4, pp. 1267-1273 (2000).
Ma Y et al. "The c-KIT mutation causing human mastocytosis is resistant to STI571 and other KIT kinase inhibitors; kinases with enzymatic site mutations show different inhibitor sensitivity profiles than wild-type kinases and those with regulatory-type mutations.", Blood, vol. 99, No. 5, pp. 1741-1744 (2002).
Heinrich M C et al. "Inhibition of KIT Tyrosine Kinase Activity: A Novel Molecular approach to the Treatment of KIT-Positive Malignancies", Journal of Clinical Oncology, vol. 20, No. 6, pp. 1692-1703 (2002).
Takeuchi K et al. "STI571 inhibits growth and adhesion of human mast cells in culture", Journal of Leukocyte Biology, vol. 74, pp. 1026-1034 (2003).
Weisberg et al., "Characterization of AMN107, a selective inhibitor of native and mutant Bcr-Abl," Cancer Cell. vol. 7, No. 2, pp. 129-141 (2005.
Giles et al., "A phase IIII study of AMN107, a novel aminopyrimidine inhibitor of bcr-abl, on a continuous daily dosing schedule in adult patients (pts) with imatinib-resistant advanced phase chronic myeloid leukemia (CML) or relapsed/refractory Philadelphia chromosome (Ph plus) acute lymphocytic leukemia (ALL)," Blood, vol. 104, No. 11, Part 1, pp. 10A-11A (2004).
Pardanani et al., "CHIC2 deletion, a surrogate for FIP1L1-PDGFRA fusion, occurs in mastocytosis associated with eosinophilia and predicts response to imatinib mesylate therapy," Blood, vol. 102, No. 9, pp. 3093-3096 (2003).
Valent P. et al "Mastocytosis: pathology, genetics and current options for therapy", Leuk Lymphoma, Jan. 2005, vol. 46(1), pp. 35-48.
Pullarkat VA, et al: Systemic mastocytosis with associated clonal hematological non-mast-cell lineage disease: analysis of clinicopathologic features and activating c-kit mutations:, American Journal Hematol., May 2003, vol. 73(1), pp. 12-17.
Horny HP, et al: "Systemic mastocytosis with associated clonal haematological non-mast cell lineage diseases: a histopathological challenge", Jun. 2004, vol. 57(6), pp. 604-608.
Lim Ken-Hong, et al: "Systemic mastocytosis in 342 consecutive adults: survival studies and prognostic factors", Blood, Jun. 4, 2009, vol. 113, No. 23, pp. 5727-5736.
Merck Manual about Mastocytosis, 2008.
Cross, et al,: "Tyrosin kinase fusion genes in chronic myeloproliferative diseases", Leukemia (2002) vol. 16, pp. 1207-1212.
Piccaluga P.P.: "Imatinib mesylate in the treatment of hematologic malignancies", Expert Opinion in Biological Therapy, 7(1), 1517-1611, 2007.
Tefferi et al: "Imatinib therapy in clonal eosinophilic disorders, including systemic mastocytosis", International Journal of Hematology, vol. 79: pp. 441-447, 2004.
U.S. Appl. No. 60/504,245, filed Sep. 19, 2003, Dimitrijevic et al.
HHMI (Howard Hughes Medical Institute) Research News, "Drug-Resistant Cancer Outwitted by Chemical Flank Attack", 3 pages, May 20, 2003.
Tian et al., "Short Communication—Activating c-kit gene mutations in human germ cell tumors", AmJ Pathol;154(6):1643-7, Jun. 1999.

* cited by examiner

PYRIMIDYLAMINOBENZAMIDE DERIVATIVES FOR SYSTEMIC MASTOCYTOSIS

This application is a continuation of U.S. patent application Ser. No. 11/911,575, which is a National Phase application of PCT/US06/16541, filed May 1, 2006, which claims benefit of U.S. Provisional Application No. 60/676,740, filed May 2, 2005.

SUMMARY OF THE INVENTION

The present invention relates to the use of pyrimidylaminobenzamide derivatives for the preparation of a drug for the treatment of systemic mastocyctosis. The present invention also relates to a method of treating systemic mastocyctosis.

BACKGROUND OF THE INVENTION

Systemic mastocytosis (SM) can be classified into indolent SM (little or no evidence of impaired organ function), aggressive SM (presence of impaired organ function), SM associated hematologic non-mast cell disease (SM-AHNMD) and mast cell leukemia. Clinical presentation in adult SM is heterogenous and includes skin disease (usually urticaria pigmentosa), mast cell mediator-release symptoms (headache, flushing, lightheadedness, syncope, anaphylaxis, etc), and direct or indirect organ damage (bone pain from lytic bone lesions, osteoporosis or bone fractures, hepatosplenomegaly, cytopenia from bone marrow involvement). In addition, around 20% of patients with SM may display significant and sometimes isolated blood eosinophilia (Tefferi and Pardanani 2004).

In general, mast cell leukemia is a terminal disease with survival measured in months and no effective therapy to date. The natural history of indolent SM is far better with median survival measured in decades and infrequent progression to aggressive SM and SM-AHNMD. Outcome in SM-AHNMD is determined by the associated AHNMD and is significantly worse than SM without AHNMD. In both indolent and aggressive SM without AHNMD, increased bone marrow mast cell and eosinophil content, elevated serum alkaline phosphatase, anemia, and hepatosplenomegaly have been associated with poor prognosis (Tefferi and Pardanani 2004). Complete histologic and clinical remission has been achieved in patients with SM associated with the FIP1L1-PDGFRα gene fusion when treated with Gleevec® (Pardanani 2003a, Pardanani 2003b).

It has now been found that pyrimidylaminobenzamide derivatives are effective against SM, especially SM associated with the FIP1L1-PDGFRα gene fusion.

The problem to be solved by the present invention is to pyrimidylaminobenzamide derivatives which are useful in the treatment of especially systemic mastocytosis, especially SM associated with the FIP1L1-PDGFRα gene fusion.

SUMMARY OF THE INVENTION

The present invention relates to the use of pyrimidylaminobenzamide compounds of formula (I) (hereinafter: "PYRIMIDYLAMINOBENZAMIDE DERIVATIVES"):

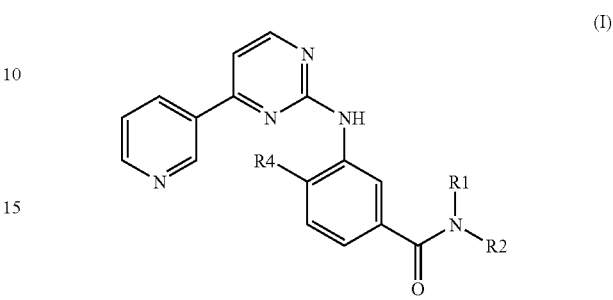

wherein $R_1$ represents hydrogen, lower alkyl, lower alkoxy-lower alkyl, acyloxy-lower alkyl, carboxy-lower alkyl, lower alkoxycarbonyl-lower alkyl, or phenyl-lower alkyl;

$R_2$ represents hydrogen, lower alkyl, optionally substituted by one or more identical or different radicals $R_3$, cycloalkyl, benzcycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted;

and $R_3$ represents hydroxy, lower alkoxy, acyloxy, carboxy, lower alkoxycarbonyl, carbamoyl, N-mono- or N,N-disubstituted carbamoyl, amino, mono- or disubstituted amino, cycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted;

or wherein $R_1$ and $R_2$ together represent alkylene with four, five or six carbon atoms optionally mono- or disubstituted by lower alkyl, cycloalkyl, heterocyclyl, phenyl, hydroxy, lower alkoxy, amino, mono- or disubstituted amino, oxo, pyridyl, pyrazinyl or pyrimidinyl; benzalkylene with four or five carbon atoms; oxaalkylene with one oxygen and three or four carbon atoms; or azaalkylene with one nitrogen and three or four carbon atoms wherein nitrogen is unsubstituted or substituted by lower alkyl, phenyl-lower alkyl, lower alkoxycarbonyl-lower alkyl, carboxy-lower alkyl, carbamoyl-lower alkyl, N-mono- or N,N-disubstituted carbamoyl-lower alkyl, cycloalkyl, lower alkoxycarbonyl, carboxy, phenyl, substituted phenyl, pyridinyl, pyrimidinyl, or pyrazinyl;

$R_4$ represents hydrogen, lower alkyl, or halogen;

and a N-oxide or a pharmaceutically acceptable salt of such a compound for the preparation of a pharmaceutical composition for the treatment of systemic mastocytosis and SM associated with the FIP1L1-PDGFRα gene fusion. The present invention further relates to use of compounds of formula I to treat or prevent systemic mastocytosis.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Any asymmetric carbon atoms may be present in the (R)-, (S)- or (R,S)-configuration, preferably in the (R)- or (S)-configuration. The compounds may thus be present as mixtures of isomers or as pure isomers, preferably as enantiomer-pure diastereomers.

The invention relates also to possible tautomers of the compounds of formula I.

Lower alkyl is preferably alkyl with from and including 1 up to and including 7, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or methyl. Preferably lower alkyl is methyl, propyl or tert-butyl.

Lower acyl is preferably formyl or lower alkylcarbonyl, in particular acetyl.

An aryl group is an aromatic radical which is bound to the molecule via a bond located at an aromatic ring carbon atom of the radical. In a preferred embodiment, aryl is an aromatic radical having 6 to 14 carbon atoms, especially phenyl, naphthyl, tetrahydronaphthyl, fluorenyl or phenanthrenyl, and is unsubstituted or substituted by one or more, preferably up to three, especially one or two substituents, especially selected from amino, mono- or disubstituted amino, halogen, lower alkyl, substituted lower alkyl, lower alkenyl, lower alkynyl, phenyl, hydroxy, etherified or esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenylthio, phenyl-lower alkylthio, lower alkylphenylthio, lower alkylsulfinyl, phenylsulfinyl, phenyl-lower alkylsulfinyl, lower alkylphenylsulfinyl, lower alkylsulfonyl, phenylsulfonyl, phenyl-lower alkylsulfonyl, lower alkylphenylsulfonyl, halogen-lower alkylmercapto, halogen-lower alkylsulfonyl, such as especially trifluoromethanesulfonyl, dihydroxybora ($-B(OH)_2$), heterocyclyl, a mono- or bicyclic heteroaryl group and lower alkylene dioxy bound at adjacent C-atoms of the ring, such as methylene dioxy. Aryl is more preferably phenyl, naphthyl or tetrahydronaphthyl, which in each case is either unsubstituted or independently substituted by one or two substituents selected from the group comprising halogen, especially fluorine, chlorine, or bromine; hydroxy; hydroxy etherified by lower alkyl, e.g. by methyl, by halogen-lower alkyl, e.g. trifluoromethyl, or by phenyl; lower alkylene dioxy bound to two adjacent C-atoms, e.g. methylenedioxy, lower alkyl, e.g. methyl or propyl; halogen-lower alkyl, e.g. trifluoromethyl; hydroxy-lower alkyl, e.g. hydroxymethyl or 2-hydroxy-2-propyl; lower alkoxy-lower alkyl; e.g. methoxymethyl or 2-methoxyethyl; lower alkoxycarbonyl-lower alkyl, e.g. methoxy-carbonylmethyl; lower alkynyl, such as 1-propynyl; esterified carboxy, especially lower alkoxycarbonyl, e.g. methoxycarbonyl, n-propoxy carbonyl or iso-propoxy carbonyl; N-mono-substituted carbamoyl, in particular carbamoyl monosubstituted by lower alkyl, e.g. methyl, n-propyl or iso-propyl; amino; lower alkylamino, e.g. methylamino; di-lower alkylamino, e.g. dimethylamino or diethylamino; lower alkylene-amino, e.g. pyrrolidino or piperidino; lower oxaalkylene-amino, e.g. morpholino, lower azaalkylene-amino, e.g. piperazino, acylamino, e.g. acetylamino or benzoylamino; lower alkylsulfonyl, e.g. methylsulfonyl; sulfamoyl; or phenylsulfonyl.

A cycloalkyl group is preferably cyclopropyl, cyclopentyl, cyclohexyl or cycloheptyl, and may be unsubstituted or substituted by one or more, especially one or two, substituents selected from the group defined above as substituents for aryl, most preferably by lower alkyl, such as methyl, lower alkoxy, such as methoxy or ethoxy, or hydroxy, and further by oxo or fused to a benzo ring, such as in benzcyclopentyl or benzcyclohexyl.

Substituted alkyl is alkyl as last defined, especially lower alkyl, preferably methyl; where one or more, especially up to three, substituents may be present, primarily from the group selected from halogen, especially fluorine, amino, N-lower alkylamino, N,N-di-lower alkylamino, N-lower alkanoylamino, hydroxy, cyano, carboxy, lower alkoxycarbonyl, and phenyl-lower alkoxycarbonyl. Trifluoromethyl is especially preferred.

Mono- or disubstituted amino is especially amino substituted by one or two radicals selected independently of one another from lower alkyl, such as methyl; hydroxy-lower alkyl, such as 2-hydroxyethyl; lower alkoxy lower alkyl, such as methoxy ethyl; phenyl-lower alkyl, such as benzyl or 2-phenylethyl; lower alkanoyl, such as acetyl; benzoyl; substituted benzoyl, wherein the phenyl radical is especially substituted by one or more, preferably one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and phenyl-lower alkoxycarbonyl, wherein the phenyl radical is unsubstituted or especially substituted by one or more, preferably one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and is preferably N-lower alkylamino, such as N-methylamino, hydroxy-lower alkylamino, such as 2-hydroxyethylamino or 2-hydroxypropyl, lower alkoxy lower alkyl, such as methoxy ethyl, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, or a substituent selected from the group comprising benzoylamino and phenyl-lower alkoxycarbonylamino, wherein the phenyl radical in each case is unsubstituted or especially substituted by nitro or amino, or also by halogen, amino, N-lower alkylamino, N,N-di-lower alkylamino, hydroxy, cyano, carboxy, lower alkoxycarbonyl, lower alkanoyl, carbamoyl or aminocarbonylamino. Disubstituted amino is also lower alkylene-amino, e.g. pyrrolidino, 2-oxopyrrolidino or piperidino; lower oxaalkylene-amino, e.g. morpholino, or lower azaalkylene-amino, e.g. piperazino or N-substituted piperazino, such as N-methylpiperazino or N-methoxycarbonylpiperazino.

Halogen is especially fluorine, chlorine, bromine, or iodine, especially fluorine, chlorine, or bromine.

Etherified hydroxy is especially $C_8$-$C_{20}$alkyloxy, such as n-decyloxy, lower alkoxy (preferred), such as methoxy, ethoxy, isopropyloxy, or tert-butyloxy, phenyl-lower alkoxy, such as benzyloxy, phenyloxy, halogen-lower alkoxy, such as trifluoromethoxy, 2,2,2-trifluoroethoxy or 1,1,2,2-tetrafluoroethoxy, or lower alkoxy which is substituted by mono- or bicyclic heteroaryl comprising one or two nitrogen atoms, preferably lower alkoxy which is substituted by imidazolyl, such as 1H-imidazol-1-yl, pyrrolyl, benzimidazolyl, such as 1-benzimidazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, indolyl or thiazolyl.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxycarbonyloxy.

Esterified carboxy is especially lower alkoxycarbonyl, such as tert-butoxycarbonyl, isopropoxycarbonyl, methoxycarbonyl or ethoxycarbonyl, phenyl-lower alkoxycarbonyl, or phenyloxycarbonyl.

Alkanoyl is primarily alkylcarbonyl, especially lower alkanoyl, e.g. acetyl.

N-Mono- or N,N-disubstituted carbamoyl is especially substituted by one or two substituents independently selected from lower alkyl, phenyl-lower alkyl and hydroxy-lower alkyl, or lower alkylene, oxa-lower alkylene or aza-lower alkylene optionally substituted at the terminal nitrogen atom.

A mono- or bicyclic heteroaryl group comprising zero, one, two or three ring nitrogen atoms and zero or one oxygen atom and zero or one sulfur atom, which groups in each case are unsubstituted or mono- or polysubstituted, refers to a heterocyclic moiety that is unsaturated in the ring binding the heteroaryl radical to the rest of the molecule in formula I and is preferably a ring, where in the binding ring, but optionally also in any annealed ring, at least one carbon atom is replaced by a heteroatom selected from the group consisting of nitrogen, oxygen and sulfur; where the binding ring preferably has 5 to 12, more preferably 5 or 6 ring atoms; and which may be unsubstituted or substituted by one or more, especially one or two, substituents selected from the group defined above as substitutents for aryl, most preferably by lower alkyl, such as methyl, lower alkoxy, such as methoxy or ethoxy, or hydroxy. Preferably the mono- or bicyclic heteroaryl group is selected from 2H-pyrrolyl, pyrrolyl, imidazolyl, benzimidazolyl, pyrazolyl, indazolyl, purinyl, pyridyl, pyrazinyl, pyrimidinyl, pyridazinyl, 4H-quinolizinyl, isoquinolyl, quinolyl, phthalazinyl, naphthyridinyl, quinoxalyl, quinazolinyl, quinnolinyl, pteridinyl, indolizinyl, 3H-indolyl, indolyl, isoindolyl, oxazolyl, isoxazolyl, thiazolyl, isothiazolyl, triazolyl, tetrazolyl, furazanyl, benzo[d]pyrazolyl, thienyl and furanyl. More preferably the mono- or bicyclic heteroaryl group is selected from the group consisting of pyrrolyl, imidazolyl, such as 1H-imidazol-1-yl, benzimidazolyl, such as 1-benzimidazolyl, indazolyl, especially 5-indazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, especially 4- or 8-quinolinyl, indolyl, especially 3-indolyl, thiazolyl, benzo[d]pyrazolyl, thienyl, and furanyl. In one preferred embodiment of the invention the pyridyl radical is substituted by hydroxy in ortho position to the nitrogen atom and hence exists at least partially in the form of the corresponding tautomer which is pyridin-(1H)2-one. In another preferred embodiment, the pyrimidinyl radical is substituted by hydroxy both in position 2 and 4 and hence exists in several tautomeric forms, e.g. as pyrimidine-(1H, 3H)2,4-dione.

Heterocyclyl is especially a five, six or seven-membered heterocyclic system with one or two heteroatoms selected from the group comprising nitrogen, oxygen, and sulfur, which may be unsaturated or wholly or partly saturated, and is unsubstituted or substituted especially by lower alkyl, such as methyl, phenyl-lower alkyl, such as benzyl, oxo, or heteroaryl, such as 2-piperazinyl; heterocyclyl is especially 2- or 3-pyrrolidinyl, 2-oxo-5-pyrrolidinyl, piperidinyl, N-benzyl-4-piperidinyl, N-lower alkyl-4-piperidinyl, N-lower alkyl-piperazinyl, morpholinyl, e.g. 2- or 3-morpholinyl, 2-oxo-1H-azepin-3-yl, 2-tetrahydrofuranyl, or 2-methyl-1,3-dioxolan-2-yl.

Salts are especially the pharmaceutically acceptable salts of compounds of formula I.

Such salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of formula I may also form internal salts.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

Compounds within the scope of formula I and the process for their manufacture are disclosed in WO 04/005281 published on Jan. 15, 2004 which is hereby incorporated into the present application by reference. A preferred compound is 4-methyl-3-[[4-(3-pyridinyl)-2-pyrimidinyl]amino]-N-[5-(4-methyl-1H-imidazol-1-yl)-3-(trifluoromethyl)phenyl] benzamide pharmaceutically acceptable salts thereof of formula (II):

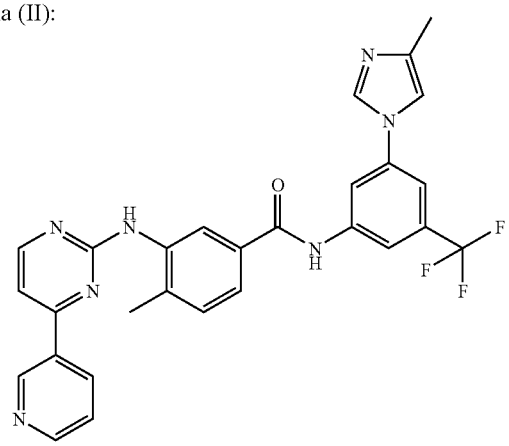

In each case where citations of patent applications or scientific publications are given in particular for the PYRIMIDYLAMINOBENZAMIDE DERIVATIVE compounds, the subject-matter of the final products, the pharmaceutical preparations and the claims are hereby incorporated into the present application by reference to these publications.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

It has now surprisingly been found that PYRIMIDYLAMINOBENZAMIDE DERIVATIVES possesses therapeutic properties, which render it particularly useful as an inhibitor of PDGFRα (platelet derived growth factor α, also abbreviated as PDGRA) and especially for the treatment and prophylaxis of FIP1L1-PDGFRα-induced diseases such as systemic mastocytosis.

FIP1L1-PDGFRα, as used hereinbefore and hereinafter, is the designation of the fusion product of the genes FIP1L1 (FIP1 like 1) with PDGFRα.

The present invention thus concerns the use of PYRIMIDYLAMINOBENZAMIDE DERIVATIVES for the preparation of a drug for the treatment of FIP1L1-PDGFRα-induced systemic mastocytosis, or other diseases associated with FIPL1-PDGFRα or similar mutations that activate PDGFRα.

Systemic Mastocytosis (SM) includes indolent SM, aggressive SM, and SM associated hematologic non-mast cell disease and mast cell leukemia.

In another embodiment, the instant invention relates to the use of PYRIMIDYLAMINOBENZAMIDE DERIVATIVES for the preparation of a pharmaceutical composition for use in treating allergic rhinitis, allergic dermatitis, drug allergy or food allergy, angioedema, urticaria, sudden infant death syndrome, bronchopulmonary aspergillosis, multiple sclerosis, or mastocytosis, more particularly for treating allergic rhinitis, allergic dermatitis, drug allergy or food allergy, angioedema, urticaria, sudden infant death syndrome, bronchopulmonary aspergillosis, multiple sclerosis, or mastocytosis with resistance to imatinib.

The term "allergic rhinitis" as used herein means any allergic reaction of the nasal mucosa. Such allegic reaction may occur, e.g., perennially, e.g. vernal conjunctivitis, or seasonally, e.g., hay fever.

The term "allergic dermatitis" as used herein means especially atopic dermatitis, allergic contact dermatitis and eczematous dermatitis, but comprises, e.g., also seborrhoeic dermatitis, Lichen planus, urticaria and acne. Atopic dermatitis as defined herein is a chronic inflammatory skin disorder seen in individuals with a hereditary predisposition to a lowered cutaneous threshold to pruritus. It is principally characterized by extreme itching, leading to scratching and rubbing that in turns results in the typical lesons of eczema. Allergic contact dermatitis as defined herein is a form of dermatitis that is due to the allergic sensitization to various substances that produce inflammatory reactions in the skin of those who have acquired hypersensitivity to the allergen as a result of previous exposure to it.

The term "drug allergy or food allergy" as used herein pertains to an allergic reaction produced by a drug or ingested antigens, such as, for example, strawberries, milk or eggs.

The term "bronchopulmonary aspergillosis" relates to an infection of the lungs with *Aspergillus*.

The term "mastocytosis" as used herein, relates to systemic mastocytosis, for example mastocytoma, and also to canine mast cell neoplasms. Mastocytosis is a myeloproliferative disorder with limited treatment options and generally a poor prognosis. The pathogenesis of mastocytosis has been attributed to constitutive activation of the receptor tyrosine kinase KIT. In a large majority of mastocytosis patients, the deregulated tyrosine kinase activity of KIT is due to a mutation within the codon 816 of the protein (D816V) which also confers resistance to imatinib or imatinib mesylate, the latter being marketed as Gleevec® in the United States or Glivec® elsewhere, in vitro and in vivo.

Mast cells play an important role as the primary effector cells in the allergic disorders mentioned herein. Antigen-specific IgE-mediated degranulation of mast cells leads to the subsequent release of chemical mediators and multiple cytokines and to leukotriene synthesis. Furthermore, mast cells are involved in the pathogenesis of multiple sclerosis.

Mast cell neoplasms occur in both humans and animals. In dogs, mast cell neoplasms are called mastocytomas, and the disease is common, representing 7%-21% of canine tumors. A distinction must be drawn between human mastocytosis, which is usually transient or indolent, and canine mast cell neoplasia, which behaves unpredictably and is often aggressive and metastatic. For instance, human solitary mastocytomas do not often metastasize; in contrast, 50% of canine mastocytomas behave in a malignant fashion, as estimated by Hottendorf & Nielsen (1969) after review of 46 published reports of tumors in 938 dogs.

Cancer in the pet population is a spontaneous disease. Pet owners, motivated by prolonging the quality of their animals' life, frequently seek out the specialized care and treatment of veterinary oncologists at private referral veterinary hospitals and veterinary teaching hospitals across the country. Therapeutic modalities of veterinary cancer patients are similar to humans, including surgery, chemotherapy, radiation therapy, and biotherapy. It has been estimated that there are 42 million dogs and approximately 20 million cats in the United States. Using crude estimates of cancer incidence, there are roughly 4 million new cancer diagnoses made in dogs and a similar number in cats made each year.

Cutaneous mast cell tumors in dogs are a common problem. Most mast cell tumors are benign and are cured with simple resection; however, if recurrent or metastatic to distant sites therapeutic options are limited. Treatment options for recurrent lesions can include external beam radiation therapy. For distant metastases or disseminated disease the use of Lomustine and vinblastine containing chemotherapy protocols have demonstrated some benefit. Sites for metastases for mast cell tumors include skin, regional lymph nodes, spleen, liver, and bone marrow.

The KIT receptor's involvement in the pathogenesis of mastocytosis is suggested by the observation that several mutations resulting in constitutive activation of KIT have been detected in a number of mast cell lines. For instance, a point mutation in human c-KIT, causing substitution of Val for Asp816 in the phosphotransferase domain and receptor autoactivation, occurs in a long-term human mast cell leukemia line (HMC-1) and in the corresponding codon in two rodent mast cell lines. Moreover, this activating mutation has been identified in situ in some cases of human mastocytosis. Two other activating mutations have been found in the intracellular juxtamembrane region of KIT, ie. the Val560Gly substitution in the human HMC-1 mast cell line, and a seven amino acid deletion (Thr573-His579) in a rodent mast cell line called FMA3.

The present invention more particularly concerns the use of PYRIMIDYLAMINOBENZAMIDE DERIVATIVES for the preparation of a drug for the treatment of systemic mastocytosis.

In another embodiment, the instant invention provides a method for treating systemic mastocytosis comprising administering to a mammal in need of such treatment a therapeutically effective amount of PYRIMIDYLAMINOBENZAMIDE DERIVATIVES, or pharmaceutically acceptable salts or prodrugs thereof.

Preferably the instant invention provides a method for treating mammals, especially humans, suffering from systemic mastocytosis comprising administering to a mammal in need of such treatment an FIP1L1-PDGFRα inhibiting amount of 4-Methyl-3-[[4-(3-pyridinyl)-2-pyrimidinyl]amino]-N-[5-(4-methyl-1H-imidazol-1-yl)-3-(trifluoromethyl)phenyl]benzamide (Compound (II)) or a pharmaceutically acceptable salt thereof.

In the present description, the term "treatment" includes both prophylactic or preventative treatment as well as curative or disease suppressive treatment, including treatment of patients at risk of contracting the disease or suspected to have contracted the disease as well as ill patients. This term further includes the treatment for the delay of progression of the disease.

The term "curative" as used herein means efficacy in treating ongoing episodes involving systemic mastocytosis.

The term "prophylactic" means the prevention of the onset or recurrence of diseases involving systemic mastocytosis.

The term "delay of progression" as used herein means administration of the active compound to patients being in a pre-stage or in an early phase of the disease to be treated, in which patients for example a pre-form of the corresponding disease is diagnosed or which patients are in a condition, e.g. during a medical treatment or a condition resulting from an accident, under which it is likely that a corresponding disease will develop.

This unforeseeable range of properties means that the use of PYRIMIDYLAMINOBENZAMIDE DERIVATIVES are of particular interest for the manufacture of a medicament for the treatment of d systemic mastocytosis.

This effect can especially be clinically relevant for patients with systemic mastocytosis.

To demonstrate that PYRIMIDYLAMINOBENZAMIDE DERIVATIVES are particularly suitable for the treatment of systemic mastocytosis with good therapeutic margin and other advantages, clinical trials can be carried out in a manner known to the skilled person.

The precise dosage of PYRIMIDYLAMINOBENZAMIDE DERIVATIVES to be employed for inhibiting systemic mastocytosis depends upon several factors including the host, the nature and the severity of the condition being treated, the mode of administration. The compound of formula I can be administered by any route including orally, parenterally, e.g., intraperitoneally, intravenously, intramuscularly, subcutaneously, intratumorally, or rectally, or enterally. Preferably the compound of formula I is administered orally, preferably at a daily dosage of 1-300 mg/kg body weight or, for most larger primates, a daily dosage of 50-5000, preferably 500-3000 mg. A preferred oral daily dosage is 1-75 mg/kg body weight or, for most larger primates, a daily dosage of 10-2000 mg, administered as a single dose or divided into multiple doses, such as twice daily dosing.

Usually, a small dose is administered initially and the dosage is gradually increased until the optimal dosage for the host under treatment is determined. The upper limit of dosage is that imposed by side effects and can be determined by trial for the host being treated.

Compounds of formula I may be combined with one or more pharmaceutically acceptable carriers and, optionally, one or more other conventional pharmaceutical adjuvants and administered enterally, e.g. orally, in the form of tablets, capsules, caplets, etc. or parenterally, e.g., intraperitoneally or intravenously, in the form of sterile injectable solutions or suspensions. The enteral and parenteral compositions may be prepared by conventional means.

The PYRIMIDYLAMINOBENZAMIDE DERIVATIVES can be used alone or combined with at least one other pharmaceutically active compound for use in these pathologies. These active compounds can be combined in the same pharmaceutical preparation or in the form of combined preparations "kit of parts" in the sense that the combination partners can be dosed independently or by use of different fixed combinations with distinguished amounts of the combination partners, i.e., simultaneously or at different time points. The parts of the kit of parts can then, e.g., be administered simultaneously or chronologically staggered, that is at different time points and with equal or different time intervals for any part of the kit of parts. Non-limiting examples of compounds which can be cited for use in combination with PYRIMIDYLAMINOBENZAMIDE DERIVATIVES are cytotoxic chemotherapy drugs, such as cytosine arabinoside, daunorubicin, doxorubicin, cyclophosphamide, VP-16, or imatinib etc. Further, PYRIMIDYLAMINOBENZAMIDE DERIVATIVES could be combined with other inhibitors of signal transduction or other oncogene-targeted drugs with the expectation that significant synergy would result.

The invention further pertains the combination of a PYRIMIDYLAMINOBENZAMIDE DERIVATIVE as described hereinbefore with imatinib for the treatment of the diseases and conditions described hereinbefore. The administration of such a combination may be affected at the same time, for instance in the form of a fixed, combined pharmaceutical composition or preparation, or sequentially or timely staggered. The administration of a PYRIMIDYLAMINOBENZAMIDE DERIVATIVE in a dosage form as described hereinbefore and of imatinib in its marketed form of GLEEVEC® in the US/GLIVEC® in Europe and with the dosages envisaged for these dosage forms is currently preferred.

The treatment of systemic mastocytosis with the above combination may be a so-called first line treatment, i.e. the treatment of a freshly diagnosed disease without any preceeding chemotherapy or the like, or it may also be a so-called second line treatment, i.e. the treatment of the disease after a preceeding treatment with imatrinib or a PYRIMIDYLAMINOBENZAMIDE DERIVATIVE, depending on the severity or stage of the disease as well as the over all condition of the patient etc.

The efficacy of PYRIMIDYLAMINOBENZAMIDE DERIVATIVES for the treatment of systemic mastocytosis is illustrated by the results of the following examples. These examples illustrate the invention without in any way limiting its scope:

IL-3 Independence Cell Proliferation Assays:

The effects of compounds on viability and proliferation of the cells is determined using the luminescent ATP Detection assay kit ATPLite™ from Perkin Elmer Life Sciences (Cat. No: 6016947) according to the instructions of the suppliers. This assay system is based on the production of light (luminescence) caused by the reaction of ATP with added luciferase and D-luciferin.

Ba/F3 FIP-PDGFRα, Ba/F3 kit D-816-V, Ba/F3 kit D-816-Y, Ba/F3 kit delVV, Ba/F3 kit R-634-W cell lines, grown in suspension in RPMI 1640 (Invitromex, Cat. No.: L0501), 10% fetal calf serum (Amimed, Cat. No.: 2-01F86-I), 2 mM L-glutamine (Gibco), are seeded into black 96-well tissue culture plates (Packard) at a density of 10000 cells per well in 50 µL complete medium immediately followed by addition of 50 µL per well serial two-fold dilutions of 2× concentrated compounds (duplicates). Cells without compound are used as a control and medium without cells is used to determine the assay background signal. After 70 h incubation (37° C., 5% $CO_2$), the cells are lysed by addition of 50 µL per well mammalian cell lysis solution (provided with the kit) and 5 min shaking in an orbital plate shaker at 700 rpm. Subsequently, 50 µL substrate solution (luciferase and D-luciferin) is added and after 5 min shaking and 10 min dark-adaptation of the plates, light emission is measured with a Packard TopCount.

The compound activity is determined as total growth inhibition (TGI) of the cell cultures and is calculated as follows: After subtraction of the background signal the signal obtained for the control cells is taken as 100%. The effect of the compound is expressed as percent reduction of the control signal. The TGI50 values are determined from the dose response curves by graphical extrapolation.

GIST882, is a human gastrointestinal stromal tumor (GIST) cell line expressing an activating KIT mutation (exon 13, K-642-E) (Tuveson D A, Willis N A, Jacks T, Griffin J D, Singer S, Fletcher C D, Fletcher J A, Demetri G D, *STI571 inactivation of the gastrointestinal stromal tumor c-KIT oncoprotein: biological and clinical implications*, Oncogene, 2001 Aug. 16; 20(36):5054-8). The GIST882 cells are cultivated in RPMI 1640 (Invitromex, Cat. No: L0501), supplemented with 15% FCS, and 2 mM glutamine (Gibco). Cell culture flasks and 96 well tissue culture plates are treated with 1.5% gelatine solution in nanopure water for 30-60 min at 37° C. prior to seeding the cells to improve adherence and cell growth. The gelatine (BIORAD, EIA purity reagent, #170-6537) is sterilized before use by heating (autoclave).

GIST882 cells are seeded into black 96-well tissue culture plates (Packard) at a density of 10000 cells per well in 50 µL complete medium and incubated for one day in order to allow for attachment of the cells. Serial two-fold dilutions of 2× concentrated compound is added (50 µL per well) in duplicates (final volume: 100 µL per well). Cells without compound are used as a control and medium without cells is used to determine the assay background signal. After 70 h incubation (37° C., 5% $CO_2$), the cells are lysed by addition of 50 µL per well mammalian cell lysis solution (provided with the kit) and 5 min shaking in an orbital plate shaker at 700 rpm. Subsequently, 50 µL substrate solution (luciferase and D-luciferin) is added and after 5 min shaking and 10 min dark-adaptation of the plates, light emission was measured with a Packard TopCount.

The compound activity is determined as total growth inhibition (TGI) of the cell cultures and is calculated as follows: After subtraction of the background signal the signal obtained for the control cells is taken as 100%. The effect of the compound is expressed as percent reduction of the control signal. The TGI50 values are determined from the dose response curves by graphical extrapolation.

Compound (II) inhibits the proliferation of GIST882 cells with a mean IC50 value of <200 nM.

Assay to Determine Effects on Kit Autophosphorylation in Cells:

The phosphorylation status of the cellular targets in lysates from cells—untreated or treated with compound—is determined with capture ELISAs. Adherent cells are grown in 96-well flat-bottom tissue culture plates close to confluency. Cells growing in suspension are seeded at 100000-150000 cells per well. After treatment with serial compound dilutions cells are washed once with PBS following cell lysis with 100 to 150 µL lysis buffer (50 mM Tris/HCl, pH 7.4, 150 mM sodium chloride, 5 mM EDTA, 1 mM EGTA, 1% NP-40, 2 mM sodium ortho-vanadate, 1 mM PMSF, 50 µg/mL aprotinin and 80 µg/mL leupeptin). Cell lysates are used immediately or stored at −20° C. 50 µL of the lysates are transferred to black ELISA plates (NUNC-Maxisorp, Cat. No.: Nr.437111) that are previously coated with a monoclonal anti-CD117 antibody obtained from Diaclone (#854.510.000) is used. For coating, the antibody is diluted in PBS and incubated with the plates overnight at 4° C. (50 µL/well). Phosphorylation of the captured Kit is detected using a commercial anti-P-Tyr Ab, labeled with alkaline phosphatase (AP), PY20 AP from Zymed, at a final concentration range between 1:3000 and 1:10000 (0.1 to 0.33 µg/ml). The second Ab is added after removal of the cell lysates. Finally, 90 µL per well of a chemiluminescent AP substrate (CDPStar RTU with Emerald II from Applied Biosystems (Cat. No.: T2388C) are added and incubated for 45 min at RT in the dark. The plates are sealed with Packard TopSeal™-A plate sealers (Cat. No. 6005185) and luminescence is quantified by measuring counts per second (CPS) with a Packard Top Count Microplate Scintillation Counter (Top Count).

The difference between the ELISA-readout (CPS) obtained with the lysates of the untreated cells and the readout for the assay-background (all components, but without cell lysate) is calculated and taken as 100% reflecting the constitutively phosphorylated Kit protein present in these cells. The activity of the compound on the Kit kinase activity is expressed as percent reduction of the Kit phosphorylation. The values for the IC50 and IC90 are determined from the dose response curves by graphical extrapolation.

Example I

A Phase II, open-label study was designed to evaluate the safety and efficacy of Compound (II) administered orally 400 mg twice daily. SM patients meeting specific disease criteria and with a clinical indication for treatment were enrolled. The results are based on preliminary data for the first 23 pts in this study. Results: The median age was 49 (range 33-78) yrs and the median time from diagnosis of SM was 27 (range 1 to 292) months. For those with data available, 13/17 pts had a c-kit D816V mutation in bone marrow cells. The median exposure to Compound (II) was 144 days. Treatment is ongoing for 18 (78%) pts; 5 (22%) discontinued, 3 (13%) for adverse events and 2 (9%) withdrew consent. Three (13%) responses were reported (2 incomplete remission and 1 minor response), based on serum tryptase, bone marrow mast cell counts and improvement of clinical symptoms. Baseline mutation data are available for 2 of the 3 responding pts and revealed the c-kit D816V mutation. These data suggest that Compound (II) has clinical activity and an acceptable safety and tolerability profile in pts with SM.

The invention claimed is:

1. A method of treating systemic mastocytosis in a patient in need thereof comprising administering to the patient 4-Methyl-3-[[4-(3-pyridinyl)-2-pyrimidinyl]amino]-N-[5-(4-methyl-1H-imidazol-1-yl)-3-(trifluoromethyl)phenyl]benzamide of formula:

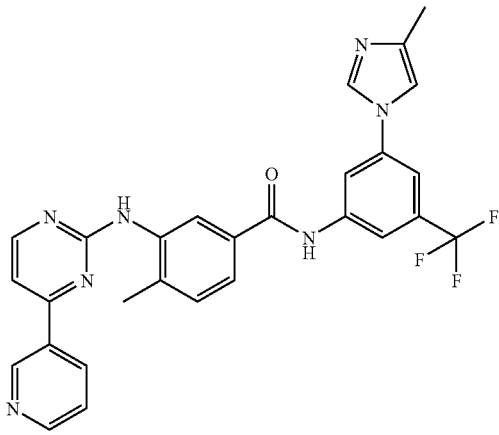 [SMILES: Cc1cn(-c2cc(NC(=O)c3ccc(C)c(Nc4nccc(-c5cccnc5)n4)c3)cc(C(F)(F)F)c2)cn1]

or a pharmaceutically acceptable salt of such a compound, wherein the systemic mastocytosis has resistance to imatinib and is associated with FIP1L1-PDGFRα.

2. A method according to claim 1 wherein the systemic mastocytosis is indolent systemic mastocytosis.

3. A method according to claim 1 wherein the systemic mastocytosis is aggressive systemic mastocytosis.

4. A method according to claim 1 wherein the systemic mastocytosis is systemic mastocytosis with associated clonal, hematologic non-mast cell lineage disease.

5. A method according to claim 1 wherein the systemic mastocytosis is systemic mastocytosis associated with mast cell leukemia.

* * * * *